United States Patent
Ito et al.

(10) Patent No.: US 10,604,823 B2
(45) Date of Patent: Mar. 31, 2020

(54) FORGED TITANIUM ALLOY MATERIAL AND METHOD FOR PRODUCING SAME, AND ULTRASONIC INSPECTION METHOD

(71) Applicant: KOBE STEEL, LTD., Kobe-shi (JP)

(72) Inventors: Yoshinori Ito, Kobe (JP); Shogo Murakami, Takasago (JP); Keiji Kinoshita, Takasago (JP)

(73) Assignee: KOBE STEEL, LTD., Kobe-shi (JP)

( * ) Notice: Subject to any disclaimer, the term of this patent is extended or adjusted under 35 U.S.C. 154(b) by 911 days.

(21) Appl. No.: 14/785,977

(22) PCT Filed: Jun. 5, 2013

(86) PCT No.: PCT/JP2013/065627
§ 371 (c)(1),
(2) Date: Oct. 21, 2015

(87) PCT Pub. No.: WO2014/196042
PCT Pub. Date: Dec. 11, 2014

(65) Prior Publication Data
US 2016/0060729 A1 Mar. 3, 2016

(51) Int. Cl.
*C22C 14/00* (2006.01)
*C22F 1/00* (2006.01)
(Continued)

(52) U.S. Cl.
CPC ............ *C22C 14/00* (2013.01); *C22F 1/00* (2013.01); *C22F 1/002* (2013.01); *C22F 1/18* (2013.01);
(Continued)

(58) Field of Classification Search
CPC .. C22C 14/00; C22F 1/00; C22F 1/002; C22F 1/18; C22F 1/183; G01N 2291/0234;
(Continued)

(56) References Cited

U.S. PATENT DOCUMENTS 3,470,034 A * 9/1969 Kastanek ............... C22F 1/183
148/670
4,799,975 A * 1/1989 Ouchi .................... C22F 1/183
148/671
(Continued)

FOREIGN PATENT DOCUMENTS

EP 1 433 863 A1 6/2004
JP 3-140447 A 6/1991
(Continued)

OTHER PUBLICATIONS

ALLVAC® TI-17 (Year: 2019).*
(Continued)

*Primary Examiner* — Veronica F Faison
(74) *Attorney, Agent, or Firm* — Oblon, McClelland, Maier & Neustadt, L.L.P.

(57) ABSTRACT

A forged titanium alloy material having a duplex grain structure composed of flat grains and non-flat grains, wherein the flat grains are crystal grains of prior-$\beta$ grains each having an aspect ratio of more than 3 and the non-flat grains are crystal grains of prior-$\beta$ grains each having an aspect ratio of 1 to 3 inclusive. The forged titanium alloy material is characterized in that the average equivalent circle diameter of the non-flat grains is 100 μm or less, flat grains each having a thicknesswise diameter of 20 to 500 μm are contained in an amount of 40 to 98%, non-flat grains each having a thicknesswise diameter of 10 to 150 μm are contained in an amount of 2 to 50%, and the flat grains each having the above-mentioned thicknesswise diameter and the non-flat grains each having the above-mentioned thicknesswise diameter are contained in the total amount of 90% or more.

6 Claims, 2 Drawing Sheets

(a)

(b)

(51) Int. Cl.
*C22F 1/18* (2006.01)
*G01N 29/04* (2006.01)
*G01N 29/11* (2006.01)

(52) U.S. Cl.
CPC ............. *C22F 1/183* (2013.01); *G01N 29/04* (2013.01); *G01N 29/11* (2013.01); *G01N 2291/0234* (2013.01); *G01N 2291/044* (2013.01); *G01N 2291/2694* (2013.01)

(58) Field of Classification Search
CPC ..... G01N 2291/044; G01N 2291/2694; G01N 29/04; G01N 29/11
See application file for complete search history.

(56) References Cited

U.S. PATENT DOCUMENTS

| | | | | |
|---|---|---|---|---|
| 5,026,520 | A * | 6/1991 | Bhowal | C22F 1/183 148/670 |
| 5,277,718 | A * | 1/1994 | Paxson | C22F 1/183 148/417 |
| 6,332,935 | B1 * | 12/2001 | Gorman | C22F 1/183 148/508 |
| 7,837,812 | B2 * | 11/2010 | Marquardt | C22C 14/00 148/671 |
| 2006/0157170 | A1 * | 7/2006 | Barbier | C22F 1/183 148/670 |
| 2007/0193018 | A1 * | 8/2007 | Davis | B21B 1/46 29/527.7 |
| 2011/0240181 | A1 * | 10/2011 | Gallois | B21K 3/00 148/670 |
| 2013/0118653 | A1 * | 5/2013 | Bryan | C22F 1/183 148/565 |

FOREIGN PATENT DOCUMENTS

| | | |
|---|---|---|
| JP | 4-276548 A | 10/1992 |
| JP | 2988269 B2 | 12/1999 |
| JP | 2006-183100 A | 7/2006 |
| JP | 2007-84865 A | 4/2007 |
| JP | 2009-299124 A | 12/2009 |
| JP | 2011-102414 A | 5/2011 |
| JP | 2011/144413 A | 7/2011 |

OTHER PUBLICATIONS

Shear-induced, solid state joining of Ti—6Al—4V and Ti17 titanium alloys (Year: 2018).*
International Search Report dated Aug. 27, 2013, in PCT/JP2013/065627 filed Jun. 5, 2013.
Written Opinion of the International Searching Authority dated Aug. 27, 2013, in PCT/JP2013/065627 filed Jun. 5, 2013.
Extended European Search Report dated Jan. 13, 2017 in Patent Application No. 13886493.9.

* cited by examiner (a)

(b)

(a)

(b)

FORGED TITANIUM ALLOY MATERIAL AND METHOD FOR PRODUCING SAME, AND ULTRASONIC INSPECTION METHOD

CROSS-REFERENCE TO RELATED APPLICATIONS

This application is a National Stage of PCT/JP2013/065627, which was filed on Jun. 5, 2013.

TECHNICAL FIELD

The present invention relates to a technique concerned with a β-forged material of an α+β type titanium alloy about which whether or not a defect is present is inspected by an ultrasonic inspection.

BACKGROUND ART

α+β Type titanium alloy, a typical example of which is Ti-6Al-4V alloy, has lightness, a high strength and a high corrosion resistance, and further has weldability, superplasticity, diffusion bondability, and various other properties to be frequently used for engine parts and others in the airplane industry. α+β Type titanium alloy has an α phase of dense hexagonal crystal (hcp structure), which is a main phase, and a β phase of body centered cubic crystal (bcc structure) that coexist stably at room temperature; and turns into a single phase of the β phase in a temperature range of the β transus temperature ($T_β$), or higher. Forged materials of α+β type titanium alloy are classified to materials based on α+β forging, which are each obtained by heating a starting material thereof into a temperature range lower than $T_β$ (α+β two-phase range) to cause the temperature of the material not to reach any temperature of $T_β$ and higher temperatures, and then forging the materials; and materials based on β forging, which are each obtained by heating a starting material thereof into a temperature range of $T_β$ (β single-phase range) and higher temperatures, and then forging the material. It is known that the two species are entirely different from each other in formed material microstructure, and accompanying the difference, the species are different from each other in material properties.

Forged titanium alloy material has an acicula α phase microstructure according to the β forging. Specifically, its microstructure is formed by as follows: a starting material thereof turns into a β single-phase in a temperature range of $T_β$ and higher temperatures; the β phase (β grains), which is in an equiaxial form, is crushed into a flat form by forging; and in a case where the material is subsequently cooled into a temperature range lower than $T_β$ and then held in this temperature range, an α phase precipitates into a membrane form along crystal grain boundaries of the β grains and subsequently another α phase precipitates into an acicula form inside the crystal grains of the β grains (the α phases are whitely represented in FIG. 2(a)). β Forging is classified into a manner of completing the forging in the β single-phase range; a manner of continuing the forging also after the temperature lowers to the outside of the β single-phase range (to the α+β two-phase range); and a manner of starting the forging after the temperature lowers to the α+β two-phase range. Furthermore, about β-forged material, the form or thickness of an α phase of crystal grain boundaries of prior β grains thereof, and the length or thickness of an acicula α phase inside the grains are varied in accordance with conditions for the forging, and conditions for cooling after the forging. Furthermore, there also exists β-forged material having no α phase in its grain boundaries. In the meantime, forged titanium alloy material has a granular α microstructure according to α+β forging (see FIG. 2(b)). In general, out of forged α+β type titanium alloy materials, forged materials obtained by β forging are better in fracture toughness than forged material obtained by α+β forging. Conversely, the forged materials obtained by α+β forging are better in fatigue strength property than the forged material obtained by β forging.

Engine parts of any airplane are required to have a high fatigue strength property and a high reliability; thus, it is inspected whether or not the parts have a defect by an ultrasonic inspection. The ultrasonic inspection is an inspection of making ultrasonic waves emitted (sent) from a probe incident to the inside of a body to be inspected from the surface thereof, and then using the same probe to receive reflected waves reflected onto a flaw and other defects therein to determine whether or not the body has an internal defect. However, an α+β type titanium alloy, in which an α phase and a β phase coexist, produces large noises caused by the material microstructure when subjected to an ultrasonic inspection whether or not the alloy is an "α+β"-forged material or β-forged material. Thus, the precision of the defect detection lowers, or a noise caused by the material microstructure is recognized as a defect by mistake, so that a problem is caused. For this reason, engine parts and others that are made of α+β type titanium alloy (hereinafter referred to as titanium alloy) have been required to be decreased in noises generated when subjected to an ultrasonic inspection, thereby being improved in ultrasonic inspectability.

Hitherto, thus, as an α+β type titanium alloy decreased in noises generated therefrom, for example, the following has been suggested: a titanium alloy rolled plate obtained by cooling a starting material thereof rapidly from the β single-phase range before the material is hot-rolled in the α+β two-phase range, thereby making the microstructure of fine, and subsequently subjecting the resultant to hot rolling and heat treatment in the α+β two-phase range, thereby yielding an equiaxial α microstructure (Patent Literature 1).

CITATION LIST

Patent Literature

[Patent Literature 1] Japanese Patent No. 2988269

SUMMARY OF INVENTION

Technical Problem

However, the above-mentioned techniques in the prior art are related to α+β type titanium alloy material based on α+β forging. In the meantime, as described above, β forged material is largely different from "α+β"-forged material in material-microstructure-formed process and the form of finally-produced material-microstructure. Thus, the two species would be different from each other in causes for noises generated when subjected to an ultrasonic inspection. Following this difference, improving methods are also different from each other therebetween. As a result, by applying the technique in Patent Literature 1 to the latter, noises cannot be decreased.

In light of these problems, the present invention has been made, and an object thereof is to provide a forged titanium alloy material that is a β-forged material of an α+β type titanium alloy which is decreased in noises generated when subjected to an ultrasonic inspection, so as to be excellent in ultrasonic inspectability while the alloy material keeps a fatigue strength property, and other mechanical properties required for parts for airplanes; a method for producing the material; and an ultrasonic inspection method.

Solution to Problem

The inventors have made eager researches to make it evident that: transmission waves are positively reflected with ease on grain boundaries of prior β grains crushed into a flat form by β forging, which each have a wide plane perpendicular to an incident direction of the transmission waves; and the reflected waves are received through a probe, so as mainly to cause noises. Furthermore, the inventors have made it evident that a β-forged material can be improved in ultrasonic inspectability while keeping a fatigue strength property and others by controlling the material microstructure appropriately.

Accordingly, the forged titanium alloy material according to the present invention is a forged material obtained by β forging and having a duplex grain microstructure comprising flat grains that are crystal grains of prior β grains, these crystal grains having an aspect ratio more than 3, and non-flat grains that are crystal grains of prior β grains, these crystal grains having an aspect ratio of 1 to 3 both inclusive, in which non-flat grains having a diameter of 10 μm or more in the thickness direction thereof, out of the non-flat grains, have an average equivalent circle diameter of 100 μm or less. The forged titanium alloy material is a material in which flat grains having a diameter of 20 to 500 μm both inclusive in the thickness direction thereof, out of the flat grains, are present in a proportion of 40 to 98% both inclusive, non-flat grains having a diameter of 10 to 150 μm both inclusive in the thickness direction thereof, out of the non-flat grains, are present in a proportion of 2 to 50% both inclusive, and the flat grains and the non-flat grains, which have the respective thickness direction diameters, are present in a total proportion of 90% or more.

The forged titanium alloy material having this structure has a microstructure in which its non-flat prior β grains having the predetermined size are present to be mixed in a proportion within the predetermined amount proportion range. Thus, the forged material is not lowered, as β-forged material, in strength. Furthermore, transmission waves are reflected on grain boundaries of the non-flat prior β grains not to be received through a probe so that noises are decreased. Accordingly, the forged material is excellent in ultrasonic inspectability.

Furthermore, it is preferred that the forged titanium alloy material according to the invention comprises a titanium alloy in which a Mo equivalent [Mo]eq represented by the following formula (1) is more than 2.7 and less than 15:

[Mo]eq=[Mo]+[Ta]/5+[Nb]/3.6+[W]/2.5+[V]/1.5+
1.25[Cr]+1.25[Ni]+1.7[Mn]+1.7[Co]+2.5[Fe] (1)

wherein each [X] represents the content by percentage (% by mass) of each of elements Xs (Xs: Mo, Ta, Nb, W, V, Cr, Ni, Mn, Co and Fe) in the titanium alloy.

According to this structure, the forged titanium alloy material turns to an α+β type titanium alloy to receive an effect of the shape of the prior β grains strongly, so that the material can have mechanical properties and ultrasonic inspectability coexisting with each other.

The forged titanium alloy material according to the invention may have a thickness of at least 50 mm. According to this structure, the material can undergo an ultrasonic inspection down to a deep portion thereof with a good precision even when made thick. Consequently, a highly reliable product can be obtained.

The forged titanium alloy material according to the invention may be produced by performing β forging. In a method according to the invention for the production of the forged titanium alloy material, the β forging comprises: heating a titanium alloy material therefor to "$T_\beta+10$"° C. or higher wherein $T_\beta$ represents the β transus temperature thereof; holding the material until the grain diameter of β crystal grains thereof turns into a range of 100 μm or more and less than 400 μm; forging the material in a temperature range of "$T_\beta-30$"° C. and higher temperatures; holding the material in this temperature range for a period of 15 seconds or longer, and shorter than a limit holding period $t_{max}$ (second (s)) represented by the following equation (2): $t_{max}=[8.0(1-T_H/1500)]^{4.76}$ (2) wherein $T_H$ represents the temperature (° C.) at the time of the holding after the forging; and cooling, immediately after the holding, the material to a temperature of "$T_\beta-150$"° C. or lower.

According to these steps, in the method for the production of the forged titanium alloy material, after β-forged, a starting material is held in the predetermined temperature range near the β transus temperature so that non-flat prior β grains grow to an appropriate extent. As a result, a forged titanium alloy material is obtained which has a duplex grain microstructure composed of these non-flat grains, and flat prior β grains generated by the forging.

The ultrasonic inspection method according to the invention for the forged titanium alloy material comprises the step of using a probe having a probe diameter ranging from 5 to 30 mm to search for a flaw of the material in a direction parallel to a direction along which the forging compression reduction of the forged titanium alloy material is largest, using ultrasonic waves having a frequency in the range ranging from 1 to 20 MHz.

According to the ultrasonic inspection method through this process, the quantity of generated noises is sufficiently small even when the forged titanium alloy material is inspected in a direction thereof along which relatively large noises may be generated. Thus, a surface of the forged titanium alloy material that has a large area can be scanned through the probe, so that the inspection can be made with ease and a high precision.

Advantageous Effects of Invention

The forged titanium alloy material according to the present invention makes it possible to detect a defect therein with a high precision by an ultrasonic inspection, and improve the reliability of engine parts of an airplane, and other products. The method according to the invention for producing a forged titanium alloy material makes it possible to produce the forged titanium alloy material easily with the above-mentioned advantageous effects. Moreover, the ultrasonic inspection method according to the invention makes it possible to inspect the forged titanium alloy material with a high precision.

DESCRIPTION OF EMBODIMENTS

Hereinafter, embodiments of the present invention will be described in detail.

[Forged Titanium Alloy Material]

In the same manner as conventional β-forged materials, the forged titanium alloy material according to the present invention is applied to engine parts of an airplane, and is particularly suitable for parts about which an internal defect needs to be inspected in an ultrasonic inspection. Specifically, the present invention is applicable to forged titanium alloy materials usable for discs or shafts. Even in a thinnest portion thereof, the thickness can be set to 50 mm or more.

The forged titanium alloy material according to the present invention includes an α+β type titanium alloy (hereinafter referred to as a titanium alloy). In the same manner as conventional β-forged materials, this material has prior β grains (β phase) and an α phase precipitating inside crystal grain boundaries or crystal grains of the prior β grains. However, about the forged titanium alloy material according to the present invention, the crystal grains of the prior β grains have a duplex grain microstructure composed of flat grains having an aspect ratio more than 3, and non-flat grains having an aspect of 1 to 3 both inclusive. Furthermore, in the forged titanium alloy material, non-flat grains having a diameter of 10 µm or more in the thickness direction thereof, out of the non-flat grains, have an average equivalent circle diameter of 100 µm or less. Moreover, flat grains having a diameter of 20 to 500 µm both inclusive in the thickness direction, out of the flat grains, are present in a proportion of 40 to 98% both inclusive, and non-flat grains having a diameter of 10 to 150 µm both inclusive in the thickness direction, out of the non-flat grains, are present in a proportion of 2 to 50% both inclusive. Furthermore, these flat grains and non-flat grains, the respective thickness direction diameters of which are in the ranges, are present in a total proportion of 90% or more.

Figure 1:
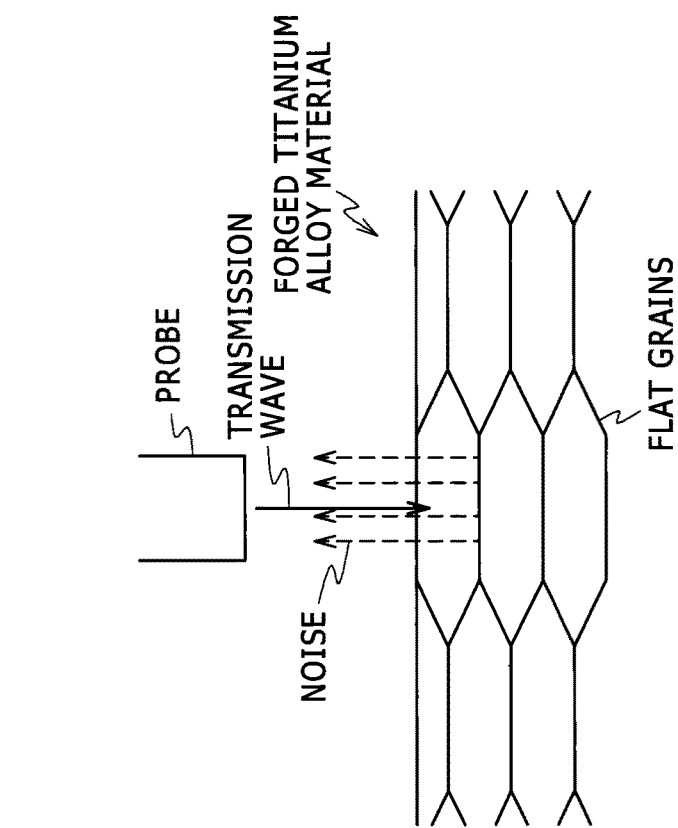
FIG. 1 are each a schematic view illustrating a state of the microstructure of a β-forged material of a titanium alloy to be a model referred to for describing a relationship between the microstructure and noises in an ultrasonic inspection.
Figure 1:
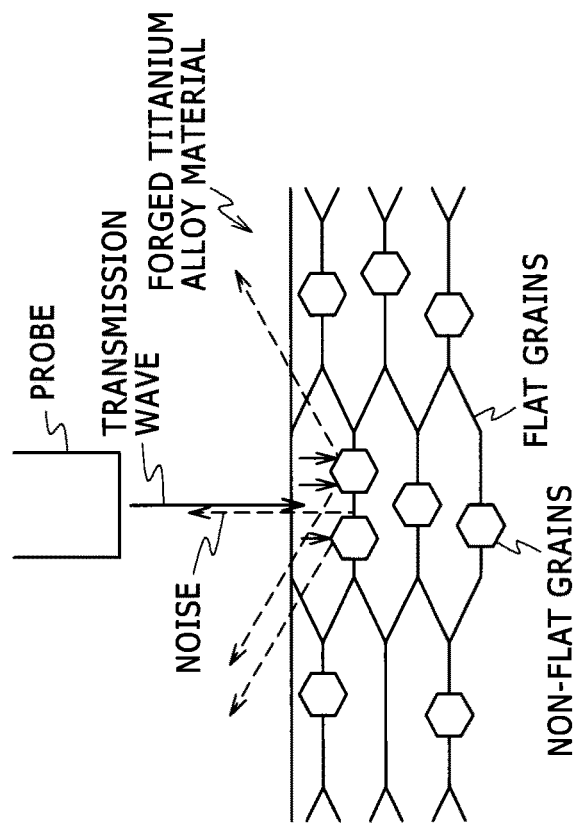
Figure 2:
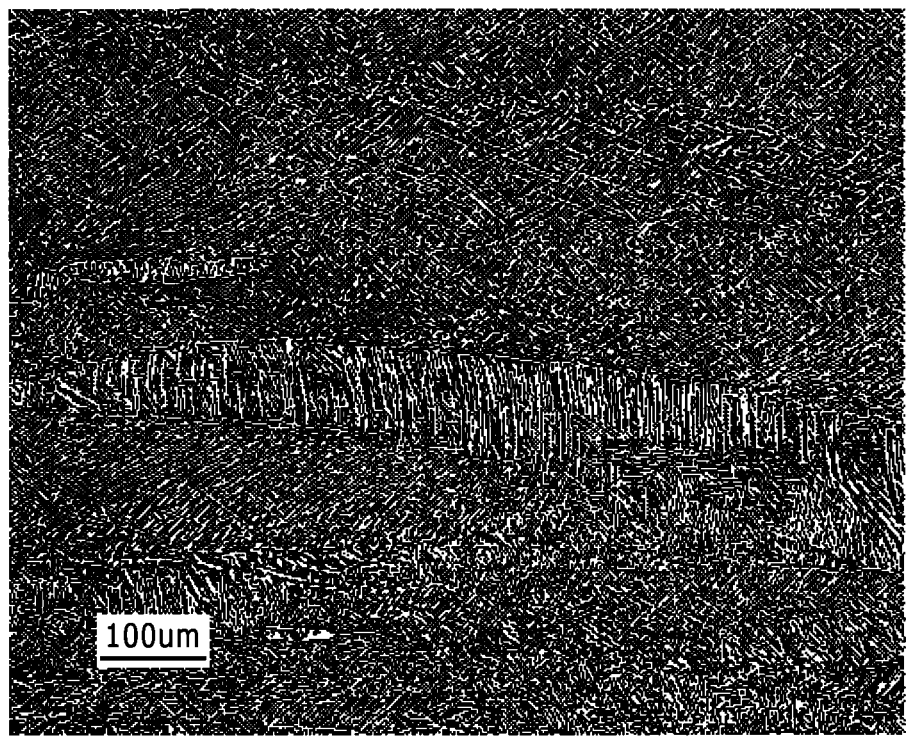
FIG. 2 are each an image photograph of the microstructure of a forged titanium alloy material, and (a) is an example of a β-forged material thereof and (b) is an example of an "α+β"-forged material thereof, respectively.
Figure 2:
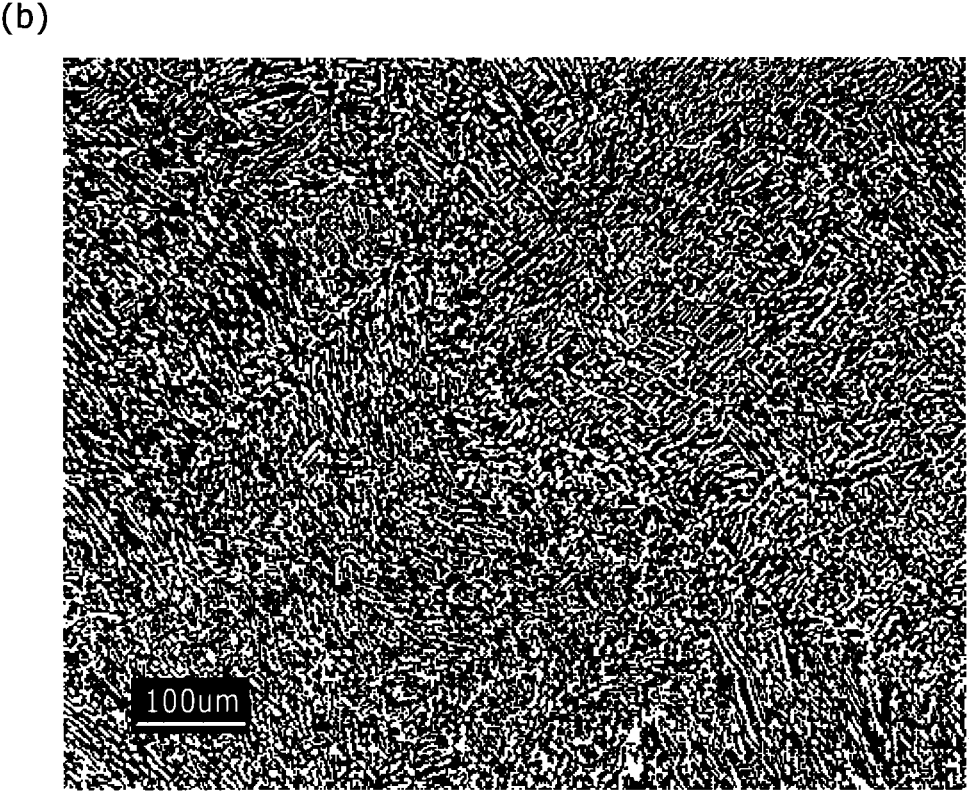

Duplex Grain Microstructure:

In the present invention, out of the prior β grains, crystal grains having an aspect ratio more than 3 are defined as flat grains; and crystal grains having an aspect ratio of 3 or less (1 or more, and 3 or less), as non-flat grains. In the invention, the aspect ratio denotes the diameter in a direction perpendicular to the thickness direction to the diameter in the thickness direction. The diameter in the thickness direction (hereinafter referred to as the thickness direction diameter) denotes the length of the crystal grain in a direction along which the dimension thereof is smallest. In the case of heating, in β forging, a titanium alloy material into a temperature range of the β transus temperature ($T_\beta$) and higher temperatures (to a β single-phase range thereof) and holding the alloy material, the alloy material turns into a single phase state of a β phase, whereby the β phase (β crystal grains) is formed in an equiaxial (non-flat) state so that the grains grow. By forging, the β crystal grains are then crushed to be deformed into a flat form spread perpendicularly to a direction along the forging (compression reduction direction). Thus, a microstructure is produced in which the β crystal grains, which have been made in a pancake form, pile onto each other. About any conventional β-forged material, a starting material thereof is forged in a β single-phase range thereof and immediately cooled so that the temperature of the material lowers into a sufficiently low temperature range less than $T_\beta$ (into an α+β two-phase range thereof); thus, as illustrated in FIG. 1(b), almost all of the β crystal grains are flat grains. In the meantime, as illustrated in FIG. 1(a), the forged titanium alloy material according to the present invention has a duplex grain microstructure of flat grains and non-flat grains. In each of FIGS. 1(a) and 1(b), α phases are present which are formed inside grains and grain boundaries of the β crystal grains (prior β grains) while the forged titanium alloy material is cooled. However, the illustration of the α phases is omitted.

Flat grains having a thickness direction diameter of 20 to 500 µm: a presence proportion of 40 to 98%:

In the same manner as conventional β-forged materials, the forged titanium alloy material according to the present invention has a high fracture toughness and fatigue strength by effect of a polycrystal microstructure of the flat-form β crystal grains (prior β grains). The reason why the aspect ratio of the prior β grains is specified to a value more than 3 is that crystal grains having an aspect ratio of 3 or less do not contribute to an improvement in the fatigue strength of the forged titanium alloy material. In the meantime, the upper limit of the aspect ratio of the flat grains of the prior β grains is not particularly stipulated. However, the aspect ratio is 30 or less under ordinary forging conditions. In other words, in order to obtain crystal grains having an aspect ratio more than 30, it is necessary to forge the alloy material until a compression reduction of about 90% or more is attained. Such a forging is unpractical. If the flat grains of the prior β grains are small in thickness direction diameter, the number of grain boundaries increases in the forged titanium alloy material in an ultrasonic inspection direction of the material. If the diameter is less than 20 µm, noises may unfavorably increase. In the meantime, flat grains having a thickness direction diameter more than 500 µm cause a fall in the fatigue strength of the forged titanium alloy material. The thickness direction of the flat grains (direction along which the dimension is smallest), which depends on the shape of the forged titanium alloy material, is consistent with the forging direction (compression reduction direction) in many cases.

The forged titanium alloy material is made better in fatigue strength as the presence proportion of flat grains having a thickness direction diameter of 20 to 500 µm both inclusive, out of the flat grains, is larger. If the proportion of the flat grains is less than 40%, the forged titanium alloy material does not sufficiently gain the fatigue-strength-improving effect based on the flat grains. Thus, the proportion of the flat grains having a size in this range is set to 40% or more, preferably 50% or more, more preferably 60% or more, most preferably 70% or more. In the meantime, even when the thickness direction diameter of the flat grains is 20 µm or more, the forged titanium alloy material is increased in noise quantity in an ultrasonic inspection if the proportion thereof is more than 98%. Thus, the proportion of the flat grains is set to 98% or less, preferably 95% or less, more preferably 90% or less, most preferably 84% or less. Accordingly, in the forged titanium alloy material according to the present invention, the flat grains of the prior β grains that have a thickness direction diameter of 20 to 500 µm both inclusive are caused to be present in a proportion of 40% to 98% both inclusive.

As described above, the flat grains are made large in thickness direction diameter, thereby decreasing the number of the grain boundaries in the ultrasonic inspection direction of the forged titanium alloy material and further improving the fracture toughness and the fatigue strength. Thus, the thickness direction diameter is preferably 30 µm or more, more preferably 70 µm or more on average. In the meantime, when the flat grains become large, the area of the grain boundaries is decreased to make it difficult that the presence proportion of the non-flat grains is ensured, as will be described later. Thus, the thickness direction diameter is preferably 170 µm or less, more preferably 130 µm or less on average. The flat grains of the prior β grains that have such a shape and a size can be obtained by adjusting the holding temperature and period when a starting material is heated into the β single-phase range before forged, so as to grow the β crystal grains into an appropriate size, and then forging the resultant at a sufficient compression reduction, thereby deforming the forged material into an aspect ratio more than 3. Furthermore, the presence proportion of the flat grains of the prior β grains can be controlled in accordance with the holding period after the forging.

Non-Flat Grains Having a Thickness Direction Diameter of 10 to 150 µm: a Presence Proportion of 2 to 50%:

In a β-forged material, ultrasonic waves made incident to the inside from the surface thereof are easily reflected on grain boundaries of prior β grains thereof. When ultrasonic waves are made incident to a conventional β-forged material in a direction parallel to the forging direction, the β-forged material, wherein prior β grains are mainly flat grains, contain many grain boundaries each having a plane perpendicular to the forging direction, as illustrated in FIG. 1(b), thereby causing the incident waves to be positively reflected. Consequently, many of the reflected waves are received by a probe to produce noises. As illustrated in FIG. 1(a), the forged titanium alloy material according to the present invention has a duplex grain microstructure in which non-flat grains are mixed with the flat grains of the prior β grains, whereby the reflected waves are dispersed not to turn to noises. Unless the non-flat grains of the prior β grains have an aspect ratio of 3 or less, the grains produce a small reflected-wave-dispersing effect so that no noise-decreasing effect is obtained. Moreover, if the thickness direction diameter of the non-flat grains of the prior β grains is less than 10 µm, the non-flat grains are small in grain boundary area so that no noise-decreasing effect is obtained. Contrarily, non-flat grains that have a thickness direction diameter more than 150 µm, out of the non-flat grains, may unfavorably cause a fall in the fatigue strength or the fracture toughness of the forged titanium alloy material.

If the proportion of the non-flat grains having a thickness direction diameter ranging from 10 to 150 µm is less than 2%, the forged titanium alloy material cannot gain a sufficient noise-decreasing effect based on the non-flat grains. Thus, the proportion of the non-flat grains is set to 2% or more, preferably 5% or more, more preferably 8% or more, even more preferably 12% or more, most preferably 16% or more. In the meantime, as the presence proportion of the non-flat grains becomes larger in the forged titanium alloy material, the proportion of the non-flat grains becomes relatively smaller so that the alloy material becomes lower in fatigue strength. Specifically, if the proportion of the non-flat grains is more than 50%, the forged titanium alloy material is short in fatigue strength. Thus, the proportion of the non-flat grains is set to 50% or less, preferably 40% or less, more preferably 30% or less. Accordingly, in the forged titanium alloy material according to the present invention, the non-flat grains of the prior β grains that have a thickness direction diameter of 10 to 150 µm both inclusive are caused to be present in a proportion of 2 to 50% both inclusive.

The flat grains, the thickness direction diameter of which is from 20 to 500 µm, and the non-flat grains, the thickness direction diameter of which is from 10 to 150 µm: a total presence proportion of 90% or more:

About the prior β grains in the forged titanium alloy material, if the presence-proportion-limited flat grains and non-flat grains, the respective thickness direction diameter of which are in the above-mentioned predetermined ranges, have a total proportion less than 90%, fine β crystal grains or coarse β crystal grains the size of which are out of these ranges are excessive so that the fatigue strength or the fracture toughness becomes insufficient or noises are increased in an ultrasonic inspection. Accordingly, in the forged titanium alloy material according to the present invention, the flat grains, the thickness direction diameter of which is from 20 to 500 µm, and the non-flat grains, that of which is from 10 to 150 µm, are caused to be present in a total proportion of 90% or more, preferably 92% or more, more preferably 94% or more.

Non-Flat Grains Having a Thickness Direction Diameter of 10 µm or More: an Average Equivalent Circle Diameter of 100 µm or Less:

As described above, ones having a large particle diameter, out of the non-flat grains, cause a fall in the fatigue strength or the fracture toughness of the forged titanium alloy material. Thus, in the forged titanium alloy material according to the present invention, the following is stipulated: the average size of grains other than fine grains having a thickness direction diameter less than 10 µm, out of the non-flat grains. Detailedly, about the non-flat grains having a thickness direction diameter of 10 µm or more, which also include non-flat grains having a thickness direction diameter more than 150 µm, the equivalent circle diameter (diameter of a circle equal in area to a cross section thereof) is set to 100 µm or less, preferably to 90 µm or less, more preferably to 80 µm or less. This manner produces the following restriction: even when the non-flat grains having a thickness direction diameter of 150 µm or less are large in particle diameter as a whole, or the proportion of the flat grains and the non-flat grains the respective thickness direction diameters of which are out of the above-mentioned predetermined range is 10% or less, a restriction is produced to cause many of the grains not to be coarse non-flat grains having a thickness direction diameter more than 150 µm. About the non-flat grains of the prior β grains that have such a shape and a size, the size and the presence proportion thereof can be controlled in accordance with the holding temperature in the β single-phase range after the forging, and the holding period corresponding to the temperature. Furthermore, by adjusting the holding temperature and period at the time of the heating into the β single-phase range before the forging, the β crystal grains are grown into an appropriate size to restrain the size of the flat grains obtained by the forging. In this way, at the time of the completion of the forging, the area of grain boundaries of the flat grains is sufficiently ensured so that the non-flat grains are formed in a sufficient number near the grain boundaries, and the presence proportion thereof can be controlled while the particle diameter is restrained.

In the present invention, the respective presence proportions of the flat grains and the non-flat grains of the prior β grains in the forged titanium alloy material each denote, in its cross section, the proportion thereof by area. The aspect ratio, the diameter and the proportion by area of the prior β grains in the forged titanium alloy material can be obtained on the basis of results obtained by cutting the forged titanium alloy material along a plane parallel to the forging direction, subjecting any one of the cross sections to polishing (mechanical-polishing or electro-polishing) for finish, corroding the cross section, and then observing this cross section. For example, viewing fields each having an area one to several millimeters square are selected from the cross section, and microstructures of the cross section are observed through an optical microscope. It is advisable to make a measurement about the length (diameter) of the prior β grains in each of the forging direction and a direction orthogonal to the forging direction, and define the flat grains and the non-flat grains on the basis of the diameter and the aspect ratio in the forging direction (thickness direction). This manner makes it possible to calculate out the average value of the respective proportions by area in the viewing fields, and the respective equivalent circle diameters of the non-flat grains.

Titanium Alloy: a Mo Equivalent More Than 2.7 and Less Than 15:

As the titanium alloy that forms the forged titanium alloy material according to the present invention, any titanium alloy is usable as far as the titanium alloy is an α+β type titanium alloy. The titanium alloy preferably has a composition in which the Mo equivalent [Mo]eq represented by an equation (1) described below is more than 2.7 and less than 15. As the Mo equivalent in the titanium alloy is made larger, the content proportion by volume of an α phase therein becomes smaller so that the titanium alloy more strongly receives the effect of the shape of the prior β grains to gain, to a further extent, the effect of improving the fracture toughness and the fatigue strength on the basis of the flat grains of the prior β grains. The Mo equivalent in the titanium alloy is more preferably 3.5 or more, even more preferably 4.5 or more. In the meantime, as the Mo equivalent [Mo]eq becomes larger in the titanium alloy, the alloying elements precipitate more easily. Thus, the microstructure may be unfavorably varied. Accordingly, the Mo equivalent is set preferably to less than 15. The Mo equivalent in the titanium alloy is more preferably 12 or less, more preferably 10 or less.

$$[Mo]eq=[Mo]+[Ta]/5+[Nb]/3.6+[W]/2.5+[V]/1.5+1.25[Cr]+1.25[Ni]+1.7[Mn]+1.7[Co]+2.5[Fe] \quad (1)$$

wherein each [X] represents the content by percentage (% by mass) of each of elements Xs (Xs: Mo, Ta, Nb, W, V, Cr, Ni, Mn, Co and Fe) in the titanium alloy.

Specific examples of such a titanium alloy include titanium alloys prescribed in AMS 4981, and AMS 4995. Titanium alloys (Ti-6Al-2Sn-4Zr-6Mo alloy, and Ti-6246 alloy) prescribed in AMS 4981 each include Al; 5.50 to 6.50% by mass; Sn: 1.75 to 2.25% by mass; Zr: 3.50 to 4.50% by mass; Mo: 5.50 to 6.50% by mass; and Ti and inevitable impurities that are the balance. The Mo equivalent calculated out from the respective average values of these elements is 6.0. The inevitable impurities generally include N: 0.04% by mass; C: 0.08% by mass; H: 0.015% by mass; Fe: 0.15% by mass; and O: 0.15% by mass.

Titanium alloys (Ti-5Al-2Sn-2Zr-4Cr-4Mo alloy and Ti-17 alloy) prescribed in AMS 4995 each include Al: 4.5 to 5.5% by mass; Sn: 1.5 to 2.5% by mass; Zr: 1.5 to 2.5% by mass; Cr: 3.5 to 4.5% by mass; Mo: 3.5 to 4.5% by mass; O: 0.08 to 0.12% by mass; and Ti and inevitable impurities that are the balance. The Mo equivalent calculated out from the respective average values of these elements is 9.5. The inevitable impurities generally include Fe; 0.03% by mass; C: 0.05% by mass; N: 0.04% by mass; and H: 0.0125% by mass.

[Method for Producing Forged Titanium Alloy Material]

The forged titanium alloy material according to the present invention is produced into a desired product form by forging an ingot made of a titanium alloy having a desired composition into a billet in a known manner (the step is called a billet forging step), optionally subjecting the billet to machining, and then β-forging the workpiece. In the billet forging step, for example, the following are performed in a described order: β forging→α+β forging→β heat treatment-→stress removing annealing→α+β forging→annealing. In the α+β forgings, the workpiece is heated into a temperature range lower than the β transus temperature (appropriately represented as $T_β$) by a temperature of about 10 to 200° C. to attain forging into a predetermined forging ratio (the ratio of the area of a cross section thereof perpendicular to the extend forging direction after the forging to that before the forging; for example, a value of 1.5); and in the β forging, the workpiece is heated into a temperature range higher than $T_β$ by a temperature of about 10 to 150° C. to attain forging into the same forging ratio. The workpiece is then cooled to room temperature in each of the forgings. It is advisable to determine whether the forging in the billet forging step is rendered α+β forging or β forging in accordance with properties required for the product. It is sufficient for the number of times of the forging to be determined in accordance with a desired diameter of the billet, and others. It is sufficient for each of the two annealing operations to be made as required. For example, the second annealing is performed to make the subsequent machining easy. Furthermore, according to the machining of the titanium alloy billet, an oxide layer, wrinkles or burrs on/in the surface are removed so that the surface roughness is adjustable. Thus, the subsequent forging (the β forging in the production of the forged titanium alloy material) is easily attained. In order to produce the forged titanium alloy material according to the present invention, the titanium alloy billet is β-forged by a method described below. Before the β forging, the titanium alloy billet may be subjected to preform forging in the α+β two-phase range to be finished into a desired shape. The forged titanium alloy material before the forging is called the titanium alloy material. In this context, as the titanium alloy material, the titanium alloy billet is used.

The method for producing the forged titanium alloy material according to the present invention includes the following operations; heating the titanium alloy material (titanium alloy billet) to "$T_β+10$"° C. or higher; holding the material until the diameter (average diameter) of β crystal grains thereof turns into a range of 100 μm or more and less than 400 μm; forging the material in a temperature range of "$T_β-30$"° C. and higher temperatures; holding the material in this temperature range for a period of 15 seconds or longer, and shorter than a limit holding period $t_{max}$ (second (s)) represented by the following equation (2); $t_{max}=[8.0(1-T_H/1500)]^{4.76}$ (2) wherein $T_H$ represents the temperature (° C.) at the time of the holding after the forging; and cooling, immediately after the holding, the material to a temperature of "$T_β-150$"° C. or lower.

"Heating Temperature Before the Forging $≥T_β+10°$ C."

In the same manner as in ordinary β forging, the heating before the forging is performed to heat the titanium alloy billet before the forging into a β single-phase range thereof to be made into a β phase single-phase. The β single-phase range is any temperature range of the β transus temperature ($T_β$) and higher temperatures. $T_β$ is a lowest temperature at which the whole (100%) of the titanium alloy billet turns into a β phase, and is varied in accordance with the composition of the titanium alloy that forms the titanium alloy billet (forged titanium alloy material). For example, $T_β$ of the titanium alloy (Ti-6246 alloy) prescribed in AMS 4981 is about 960° C., and $T_β$ of the titanium alloy (Ti-17 alloy) prescribed in AMS 4995 is about 890° C. In the present invention, the titanium alloy billet is surely made into the β phase single-phase down to a deep portion thereof, and further the forging thereof is completed in a temperature range of "$T_\beta-30$"° C. and higher temperatures. Furthermore, the resultant workpiece is subsequently held at the same temperature for a predetermined period. In the meantime, as the titanium alloy billet becomes higher in temperature in the β single-phase range, the growth rate of crystal grains in the β phase becomes larger so that the control of the grain diameter of the crystals becomes more difficult. Moreover, when the temperature exceeds "$T_\beta+15$"° C., a thick oxide scale is easily produced in the surface. Thus, it becomes necessary to remove the scale after the forging. Thus, the heating temperature is preferably "$T_\beta+150$"° C. or lower. Additionally, if the heating temperature before the forging is too high, the temperature at the time of the completion of the forging becomes high. Consequently, as will be described later, it is feared that the β crystal grains (non-flat grains) grow excessive until the workpiece is cooled to the outside of the temperature range of "$T_\beta-30$"° C. and higher temperatures, that is, to a temperature lower than "$T_\beta-30$"° C., as will be described later.

After the titanium alloy billet is heated to be caused to reach to the β single-phase range, the billet is held for a predetermined period before the start of the forging to cause the β crystal grains to grow into an appropriate size, specifically, a size within a diameter range of 100 μm or more and less than 400 μm. The holding period is varied in accordance with the holding temperature of the titanium alloy billet. For example, it is advisable to hold the billet at 1000° C. for about 5 to 60 minutes. After a desired β crystal grain microstructure is once formed in the titanium alloy billet, the temperature of the billet may lower to a temperature lower than "$T_\beta+10$"° C. before the forging. As will be described later, this temperature is set to make it possible to hold the billet in the temperature range of "$T_\beta-30$"° C. and higher temperatures till the completion of the forging and further the end of the subsequent holding period.

"Forging Temperature $\geq T_\beta-30$° C."

The titanium alloy billet heated and held for the predetermined period is forged to be made into a product shape. A tool used for the forging is preferably heated to 400° C. or higher, and more preferably heated to the forging temperature (the temperature of the titanium alloy billet). The use of the thus heated tool makes it possible to complete the forging in the state that without cooling the surface of the titanium alloy billet that is being forged excessively earlier than the inside thereof, the vicinity of the surface is kept at a temperature of "$T_\beta-30$"° C. or higher. When the forging of the titanium alloy billet is completed in the temperature range lower than "$T_\beta-30$"° C., no non-flat grains are subsequently formed, as will be described later. The temperature for the completion of the forging is preferably "$T_\beta-10$"° C. or higher, more preferably a temperature higher than $T_\beta$. It is sufficient for any portion of the product of the forged titanium alloy material to be held in the temperature range of "$T_\beta-30$"° C. and higher temperatures till the completion of the forging, and further the end of the holding which will be detailed later. No especial limitation is imposed onto the temperature of a surface layer and any excess thickness portion thereof (any portion thereof other than the portion of the product) that should be removed after the forging (cooling).

The reduction ratio (compression reduction) in the forging is not particularly limited, and thus the forging can be attained under the same conditions as used for ordinary finish forging. In an example of forging the billet that is a columnar billet, using a tool having a flat plane, in order to render the β crystal grains flat grains having an aspect ratio more than 3, it is preferred to apply, thereto, forging giving a compression reduction of 45% or more, preferably 55% or more, or forging corresponding thereto. About the shift speed of the tool to the titanium alloy billet, it is also preferred to set the strain rate into the range of $10^{-3}$ to 10 (1/s).

"Holding Period (Seconds) at the Temperature $T_H$ (° C.) ($\geq T_\beta-30$)° C. after the Forging: 15 or more, and Less Than $[8.0(1-T_H/1500)]^{4.76}$"

After the titanium alloy billet is forged, the billet is continuously held at a temperature of "$T_\beta-30$"° C., or higher for a predetermined period. By this holding of the forged titanium alloy billet in the temperature range of "$T_\beta-30$"° C. and higher temperatures, non-flat β crystal grains (non-flat grains) are newly formed separately from the β crystal grains that have been rendered flat grains by the forging. When the titanium alloy is cooled to a temperature lower than the above-mentioned temperature range, the formation and growth of the β crystal grains are substantially stopped. Thus, even when the titanium alloy billet is held into the temperature range lower than "$T_\beta-30$"° C. after the forging, the advantageous effects of the present invention cannot be obtained. Contrarily, a thick and continuous α phase precipitates in grain boundaries of the prior β grains so that the resultant may be unfavorably deteriorated in fatigue strength. The holding temperature after the forging is preferably "$T_\beta-10$"° C. or higher, more preferably a temperature higher than $T_\beta$. In the meantime, when the holding temperature after the forging becomes high, the rate at which the non-flat grains are formed becomes large so that the size or the presence ratio thereof is not easily controlled. Thus, the temperature is preferably 1150° C. or lower. When the titanium alloy is one having a temperature $T_\beta$ lower than 1000° C., the temperature is more preferably "$T_\beta+150$"° C. or lower.

If the holding period after the forging is less than 15 seconds, the size (thickness direction diameter) or the presence ratio of the non-flat grains is insufficient so that the noise-decreasing effect based on the non-flat grains cannot be obtained in an ultrasonic inspection. Accordingly, the holding period at a temperature of "$T_\beta-30$"° C., or higher after the forging is set to 15 seconds or more, preferably to 20 seconds or more, more preferably to 30 seconds or more. In the meantime, with the lapse of the holding period, the grain diameter of the non-flat grains becomes larger, so that the presence proportion thereof increases while that of the flat grains decreases relatively. Thus, if held in this temperature range for an excessively long period, the forged titanium alloy material is lowered in fatigue strength.

The growth rate of the β crystal grains depends on the holding temperature. As the temperature is higher, the growth rate is larger. Such a rate behavior is presumed on the basis of the diffusion behavior of atoms therein. Thus, a relational expression between the temperature T (° C.), and the period t (seconds) until the β crystal grains grow so that the presence ratio thereof reaches to a ratio is represented as the following equation (3), the expression being based on a diffusion equation representing the easiness of the diffusion of atoms:

$$t=[b(1-T/a)]^n \text{ wherein } a, b \text{ and } n \text{ are each a constant.} \quad (3)$$

Through experiments, the inventors have obtained the constants a, b and n by measuring the holding period (limit holding period $t_{max}$) while the holding temperature $T_H$ (° C.) of a forged titanium alloy billet is varied, this holding period being a period until the average equivalent circle diameter of non-flat grains of the billet reaches to 100 μm; and then inserting the measured value into the equation (3). As a result, a is 1500, b is 8.0 and n is 4.76, and then the following equation (2) for calculating out the limit holding period $t_{max}$ has been obtained.

$$t_{max}=[8.0(1-T_H/1500)]^{4.76} \quad (2)$$

Accordingly, the holding period at a temperature of "$T_\beta$-30"° C., or higher after the forging is made shorter than the limit holding period $t_{max}$, which is represented by the equation (2), on the basis of the holding temperature $T_H$. According to the equation (2), the limit holding period $t_{max}$ becomes shorter as the holding temperature $T_H$ becomes higher. Thus, $t_{max}$ is calculated out on the basis of a highest temperature at the time of the completion of the forging as the holding temperature $T_H$.

Immediately after the elapse of the above-mentioned holding period, the forged titanium alloy billet is cooled to a temperature of "$T_\beta$-150"° C. or lower, thereby putting the billet to the outside of the β single-phase range (into the α+β two-phase range) to stop the growth of the non-flat β crystal grains and further restraining any thick and continuous α phase in the grain boundaries of the prior β grains. In this way, the resultant forged titanium alloy material is prevented from being deteriorated in fatigue strength. For this purpose, the cooling rate after the holding is preferably 10° C./min or more, more preferably 50° C./min or more. In the meantime, the upper limit of the cooling rate is not particularly limited, and thus the rate is practically 500° C./min or less. The cooling rate is also preferred in order to make any acicula α phase in the grains long to improve the fracture toughness. The cooling method may be a known method such as air cooling, ventilation, water cooling, hot water cooling or oil cooling. The cooling rate in the temperature range lower than "$T_\beta$-150"° C. is not particularly limited. Thus, it is advisable to set the temperature in accordance with other required properties.

As required, the resultant forged titanium alloy material is subjected to heat treatment processing by solution heat treatment and ageing treatment in a known manner, and further subjected to machining to remove the oxide layer or the excess thickness portion. The forged titanium alloy material is then subjected to an ultrasonic inspection described below. Specifically, preferably, a portion thereof having a thickness of 1 mm or more from the surface thereof is taken away, and this portion is made flat and smooth into a surface roughness of 6.3 S or more; and then the portion is subjected to the ultrasonic inspection. Thereafter, the forged titanium alloy material is optionally again subjected to machining to be made into a product such as an engine part. These treatments can be conducted in a known manner.

[Ultrasonic Inspection Method]

An ultrasonic inspection method for the forged titanium alloy material according to the present invention may be performed in a known manner. A probe therefor is selected from probes each having a probe diameter ranging from 5 to 30 mm. Ultrasonic waves (transmission waves) having a frequency ranging from 1 to 20 MHz are used. It is preferred that the probe diameter is 10 mm or more and the frequency of the ultrasonic waves is 15 MHz or less. It is also preferred to make the inspection by an immersion probe inspection method high in defect-detecting resolution. The forged titanium alloy material according to the present invention can be supplied to an ultrasonic inspection in which a flaw is searched for in directions including a direction parallel to a direction along which the forging compression reduction in the forging is largest. The direction for the ultrasonic inspection denotes a direction in which the transmission waves advance (direction in which the waves are transmitted through the inside of the forged titanium alloy material) (see FIG. 1). In the forged titanium alloy material, noises tend to be generated in a largest quantity in the direction along which the forging compression reduction is largest. Even when a flaw is searched for in the forged titanium alloy material according to the present invention along this direction, the quantity of noises generated is sufficiently small so that the material can be inspected with a high precision. Moreover, the forged titanium alloy material is smallest in thickness along this direction in many cases. Thus, the material can be inspected down to a deep portion thereof with a good precision. Furthermore, surfaces thereof perpendicular to this direction, in which the probe is scanned, are wide in many cases. Thus, the material is easily inspected. It is preferred that in accordance with the shape of the forged titanium alloy material (product), a flaw can be searched for in this single direction, or further the material can be inspected two or more times in total while the scanning direction is changed. Furthermore, in accordance with the thickness (length in the transmission wave advancing direction) of the forged titanium alloy material, the transmission waves may be made incident thereto from a reverse direction.

EXAMPLES

The above has described embodiments for carrying out the present invention. The following will specifically describe working examples in which the advantageous effects of the invention have been verified while compared with comparative examples that do not satisfy the requirements of the invention. The invention is not limited by these working examples, and thus the examples may be carried out in the state that any modification is added thereto within the scope recited in the claims. These modified examples are each included in the technical scope of the invention.

[Production of Test Specimens]

As titanium alloy materials, the following were used: billets each having a diameter of 120 mm and obtained by cutting a Ti-6246 alloy prescribed in AMS 4981 ($T_\beta$: 960° C.) into a length of 180 mm in the length direction (axial direction).

β-Forging:

The titanium alloy billets were each held in a furnace at 920° C. for 2 hours to make the temperature distribution of the inside of the billet constant, and then heated to a forging temperature shown in Table 1. The billet was held at the forging temperature until β-crystals thereof were made into an average grain diameter shown in Table 1, and then taken away from the furnace. A tool heated beforehand to the forging temperature through a low-frequency heating device was used to forge the billet. In order to make the β crystal into the average grain diameter shown in Table 1, the period for the holding was obtained by using a titanium alloy material having the same shape as the forged titanium alloy material to make a preliminary experiment at the holding temperature (forging temperature), and measuring the average grain diameter of the β crystals from a microstructure photograph thereof that was obtained through an optical microscope by a microtomy. Using a tool having paired parts each having a flat surface, the forging was attained at a tool shift speed shown in Table 1 and a compression reduction of 67% to set the axial direction of the billet to a deforming direction (compression reduction direction) (the length of the material after the forging: 60 mm). About Test Specimen No. 3, about which the forging temperature was set to a temperature lower than $T_\beta$, the titanium alloy billet was heated to 1000° C., held until the billet was made into one of the β crystal grain diameters shown in Table 1 equivalently to the other test specimens, taken out from the furnace, cooled with air down to one of the forging temperatures shown in Table 1, and then forged.

After each of the billets was forged, the load onto the tool was removed, and the upper and lower surfaces of the titanium alloy billet were sandwiched between the tool parts heated to the forging temperature, and further side surfaces of the titanium alloy billet were covered with a heat insulator to hold the billet until a holding period after the forging that is shown in Table 1 lapsed from the completion of the forging. Immediately after the elapse, the billet was taken out and then cooled to room temperature to yield a forged titanium alloy material. Test specimen No. 6 was cooled with air while the other test specimens were cooled with water. About each of the titanium alloy billets, at the time of each of the heating, the holding and the forging, the forging temperature and others were controlled by using a thermocouple to measure the respective temperatures of ½·H, and ¼·D positions (wherein H: the thickness of the forged material; and D: the diameter of the forged material) thereof, that is, the temperatures of the respective middle positions of the forged material in the thickness direction and in the radius direction. Individual cooling rates shown in Table 1 after the forging were each measured through a preliminary experiment. Specifically, a titanium alloy material having the same shape as each of the forged titanium alloy materials was prepared, and then the thermocouple was inserted into each of the ½·H and ¼·D positions thereof. The titanium alloy material was heated to 1050° C., held, and then cooled with air and water to gain a cooling curve. Thereafter, on the supposition that the cooling rate was constant from the period when the temperature reached to 900° C. to that when the temperature reached to 700° C., the cooling rate was calculated out. Under a condition that the forging temperature was regarded as the holding temperature $T_H$ after the forging, the limit holding period $t_{max}$ was calculated out in accordance with the equation (2). The period is also shown in Table 1.

Heat Treatment:

Each of the forged titanium alloy materials cooled to room temperature was heated to 935° C., which is lower than $T_\beta$ (in the α+β two-phase range), held for 2 hours, and then cooled at 30° C./min. After this solution heat treatment, an ageing treatment was conducted in which the alloy material was held at 595° C. for 8 hours, and cooled to room temperature at 35° C./min. In this way, each of the test specimens was obtained.

Observation of Each Material Microstructure:

From each of the test specimens, a small test piece which was in the form of a cube 15 mm square and which contained the ½·H and ¼·D positions was cut away. In order to make the observation of prior β grains thereof easy, a heat treatment was conducted in which the test piece was heated to 900° C., which is lower than $T_\beta$ (in the α+β two-phase range), held for 30 minutes, and cooled with air. By such a heat treatment in the α+β two-phase range, the β grains undergo neither recrystallization nor grain growth, and further the area proportion of an acicula α phase inside the prior β grains is lowered while the shape of the prior β grains is kept. Consequently, the observation of the prior β grains becomes easy. From the small piece subjected to the heat treatment, cross sections were cut away which were parallel, respectively, to the forging direction and the radius direction of the test specimen. The cross sections were mechanically polished with an emery paper piece, finish-polished with diamond abrasive grains, and then corroded with a nitrohydrofluoric acid solution. The cross sections were then supplied to microstructure observation. The microstructure observation was made through an optical microscope. A viewing filed of 3200 μm×2000 μm size of each of the cross sections was panoramically observed at a multiplying power of 100. About the prior β grains, the aspect ratio and the diameter in the thickness direction (axial direction) were obtained. On the basis of the aspect ratio, flat grains and non-flat grains were detected. The respective area proportions of flat grains and non-flat grains each having the thickness direction diameter satisfying the requirements of the present invention, out of the flat grains and non-flat grains, were obtained. Furthermore, calculations were made about the average of the thickness direction diameters of flat grains having a thickness direction diameter of 20 μm or more, out of the flat grains; and the average of the equivalent circle diameters of non-flat grains having a thickness direction diameter of 10 μm or more, out of the non-flat grains. These values are shown in Table 1.

[Evaluation]

Ultrasonic Inspectability:

From each of the specimens, a test piece in the form of a cube 53 mm square was cut out, and subjected to an ultrasonic inspection using an immersion probe inspection method. A probe having a probe diameter of 19.05 mm and a focus distance of 152.4 mm was used. Ultrasonic waves having a frequency of 5 MHz were rendered transmission waves, and the water distance (the distance from the probe to a surface of the test piece) was set to 160 mm. A standardizing test piece was used to adjust the sensitivity to set the intensity of a reflection from a flat-bottomed hole having a diameter of 0.62 mm to 80%. Thereafter, using, as an inspection area, a central area having a size of 40 mm×40 mm in the test piece surface (surface perpendicular to the forging direction), the ultrasonic inspection was made in a direction parallel to the forging direction (axial direction of the specimen) while the probe was shifted and scanned. In this way, a C scope was obtained.

The C scope was a two-dimensionally demonstrated flaw-searched result obtained by shifting and scanning the probe along the surface of the specimen in the state of making the water distance constant, and extracting a maximum noise intensity value in a flaw-searching depth range detected through the probe in each of the surface-scanned points. Table 1 shows a maximum noise detected through the probe shifted and scanned in each of the test pieces. When the test piece gave a value of 35% or less, the test piece was judged to be acceptable.

Fatigue Property:

As a mechanical property of each of the forged titanium alloy materials, the fatigue strength was evaluated. From the ½·H and ¼·D positions of the test specimen, a fatigue test piece was cut out to make the circumferential (tangential line) direction of the test piece parallel to the load axis. At room temperature, the test piece was subjected to a low-cycle fatigue test in accordance with E466 of the ASTM standard under load-control at a maximum load of 1000 MPa and a stress ratio of 0, using trapezoidal waves until the fatigue test piece was fractured. The fracture cycle number thereof was calculated out as a value normalized by use of Test Specimen No. 7 as standard (1) (the resultant value was divided by the fracture cycle number of Test Specimen No.

7). The result is shown in Table 1. When the test specimen gave a value of 0.5 or more, the test specimen was judged to be acceptable.

grains, became large in proportion, and the average equivalent circle diameter was excessive. Accordingly, Test Specimens Nos. 8 and 9 were low in generated noise quantity.

TABLE 1

| Test Specimen Classification | No. | β grain diameter (μm) before forging | Forging conditions | | | | | Flat grain area proportion (%) | Non-flat grain area proportion (%) | β crystal grains | | Ultrasonic inspectability Maximum noise (%) | Fatigue property Fracture cycle number ratio |
| | | | Forging temperature (° C.) | Tool shift rate (mm/min) | Holding period (s) after forging | Limit holding period (s) | Cooling rate (° C./min) | | | Total area proportion (%) | Flat grain thickness direction diameter (μm) | Non-flat grain average equivalent circle diameter (μm) | | |
|---|---|---|---|---|---|---|---|---|---|---|---|---|---|---|
| Examples | 1 | 200 | 1000 | 1800 | 40 | 106 | 450 | 76 | 18 | 94 | 85 | 74 | 19 | 1.0 |
| | 2 | 350 | 1000 | 1800 | 50 | 106 | 450 | 86 | 9 | 95 | 120 | 86 | 29 | 1.0 |
| | 3 | 200 | 950 | 1800 | 50 | 167 | 450 | 84 | 10 | 94 | 82 | 72 | 22 | 1.0 |
| | 4 | 200 | 970 | 1800 | 120 | 140 | 450 | 77 | 18 | 95 | 80 | 90 | 19 | 0.9 |
| | 5 | 200 | 1000 | 180 | 50 | 106 | 450 | 70 | 22 | 92 | 87 | 80 | 20 | 0.9 |
| | 6 | 200 | 980 | 1800 | 50 | 128 | 60 | 83 | 13 | 96 | 85 | 70 | 20 | 1.0 |
| Comparative Examples | 7 | 800* | 1000 | 1800 | 50 | 106 | 450 | 92 | 1* | 93 | 190 | 95 | 40 | 1.0 |
| | 8 | 800* | 1010 | 1800 | 150* | 96 | 450 | 60 | 28 | 88* | 195 | 170* | 29 | 0.4 |
| | 9 | 800* | 1050 | 1800 | 240* | 64 | 450 | 15* | 65* | 80* | 200 | 240* | 22 | 0.2 |
| | 10 | 700* | 1000 | 1800 | 10* | 106 | 450 | 95 | 0.5* | 95.5 | 180 | 60 | 50 | 1.0 |

*Out of the range
Each underline is drawn below a value that does not satisfy the acceptance standard.

As shown in Table 1, Test Specimen No. 7 was forged after β crystal grains were grown into a size larger than the range in the present invention in the β single-phase range before the forging. Thus, sufficiently large flat grains of prior β grains were produced. Furthermore, the holding period after the forging was within the range in the invention, and thus the presence proportion (area proportion) thereof was sufficiently kept. As a result, about Test Specimen No. 7, the fatigue strength was high. However, the area of grain boundaries of the flat grains was small so that the number of non-flat grains was small, and the area proportion thereof was short. Consequently, the noise-decreasing effect was insufficient in the ultrasonic inspection.

By contrast, in each of Test Specimens Nos. 1 to 6, β crystal grains were grown by the producing method according to the present invention, that is, by restricting the β crystal grains into a grain diameter in the predetermined range in the β single-phase range before the forging; and after the forging, the temperature thereof was kept for a period in the predetermined range. In this manner, the test specimen was a working example in which non-flat grains of the prior β grains were grown into an appropriate size, and further the respective presence proportions of the non-flat grains and the flat grains satisfied the ranges of the forged titanium alloy material according to the present invention. As a result, Test Specimens Nos. 1 to 3, and 6 were equivalent in fatigue strength to Test Specimen No. 7. Test Specimens Nos. 4 and 5 were slightly lower in fatigue strength than Test Specimen No. 7. As described herein, these test specimens each kept mechanical properties necessary for engine parts and others of airplanes even when the non-flat grains of the prior β grains were small. Furthermore, these test specimens each showed an excellent ultrasonic inspectability.

In the meantime, about Test Specimens Nos. 8 and 9, their titanium alloy material was excessively long held after forged, so that non-flat grains were excessively grown. Moreover, grains having a thickness direction diameter more than the range in the present invention, out of the non-flat grains, became large in proportion, and the average equivalent circle diameter was excessive. Accordingly, Test Specimens Nos. 8 and 9 were low in generated noise quantity. However, these test specimens became far lower in fatigue strength than Test Specimen No. 7 although, in the former specimens, β crystal grains were grown into a larger size than the range in the invention to form large flat grains in the same way as in Test Specimen No. 7. In particular, in Test Specimen No. 9, the presence proportion of the flat grains was largely decreased so that the fatigue strength was remarkably lowered. Moreover, in Test Specimen No. 10, the flat grains were large and further the holding period after the forging was short in the same way as in Test Specimen No. 7. Thus, in the former specimen, the non-flat grains were particularly small in proportion, and noises were largely generated.

The invention claimed is:
1. A process for producing a forged titanium alloy material, the process comprising performing a β forging comprising:
   (i) heating a titanium alloy material to "$T_\beta+10$" ° C. or higher, wherein $T_\beta$ represents a β transus temperature of the titanium alloy material, to obtain a heated titanium alloy material;
   (ii) maintaining the heated titanium alloy material at the "$T_\beta+10$" ° C. or higher until a grain diameter of β crystal grains in the titanium alloy material ranges from 100 μm or more to less than 400 μm, to obtain a heated and maintained titanium alloy material;
   (iii) forging the heated and maintained titanium alloy material in a temperature range of "$T_\beta-30$" ° C. and higher, to obtain a pressed titanium alloy material;
   (iv) holding the pressed titanium alloy material in the "$T_\beta-30$" ° C. and higher temperature range for a period of 15 seconds or longer, and shorter than a limit holding period $t_{max}$ (second(s)) represented by equation (2):

$$t_{max}=[8.0(1-T_H/1500)]^{4.76} \qquad (2)$$

in which $T_H$ represents a temperature (° C.) at the time of the holding after the forging, to obtain a pressed and held titanium alloy material; and (v) cooling, immediately after the holding, the pressed and held titanium alloy material to a temperature of "$T_\beta$ −150" ° C. or lower to obtain the forged titanium alloy material, wherein:

the forged titanium alloy material has a duplex grain microstructure comprising flat crystal grains that are crystal grains of prior β grains, said flat crystal grains having an aspect ratio of more than 3, and non-flat crystal grains that are crystal grains of prior β grains, said non-flat crystal grains having an aspect ratio of 1 to 3;

non-flat grains having a diameter of 10 μm or more in a thickness direction thereof have an average equivalent circle diameter of 100 μm or less;

flat grains having a diameter of 20 to 500 μm in a thickness direction thereof are present in a proportion of 40 to 98% relative to 100% of the flat crystal grains;

non-flat grains having a diameter of 10 to 150 μm in a thickness direction thereof are present in a proportion of 2 to 50% relative to 100% of the non-flat crystal grains; and the flat crystal grains and the non-flat crystal grains are present in a total proportion of 90% or more in the forged titanium alloy.

2. The process according to claim 1, wherein the forged titanium alloy material comprises a titanium alloy in which a Mo equivalent [Mo]eq represented by formula (1) is more than 2.7 and less than 15:

[Mo]eq=[Mo]+[Ta]/5+[Nb]/3.6+[W]/2.5+[V]/1.5+
1.25[Cr]+1.25[Ni]+1.7[Mn]+1.7[Co]+2.5[Fe]   (1)

wherein each [X] represents a content by percentage (% by mass) of element X in the titanium alloy.

3. The process according to claim 1, wherein the forged titanium alloy material has a thickness of at least 50 mm.

4. The process according to claim 2, wherein the forged alloy material has a thickness of at least 50 mm.

5. The process according to claim 1, wherein:

the heating of the titanium alloy material occurs at a temperature ranging from "$T_\beta$+10" ° C. to "$T_\beta$+150" ° C., wherein $T_\beta$ represents a β transus temperature of the titanium alloy material;

the maintaining of the heated titanium alloy material occurs at the temperature ranging from the "$T_\beta$+10" ° C. to the "$T_\beta$+150" ° C.;

the forging of the heated and maintained titanium alloy material occurs in a temperature range of "$T_\beta$−10" ° C. and higher;

the holding of the pressed titanium alloy material occurs in the "$T_\beta$−10" ° C. and higher temperature range for the period of 15 seconds or longer, and shorter than the limit holding period $t_{max}$ (second(s)) represented by equation (2):

$$t_{max}=[8.0(1-T_H/1500)]^{4.76} \qquad (2)$$

wherein $T_H$ represents a temperature (° C.) at the time of the holding after the forging; and the cooling, immediately after the holding, of the pressed and held titanium alloy material occurs at the temperature of "$T_\beta$−150" ° C. or lower such that a cooling rate is 10° C./min or more.

6. An ultrasonic inspection method, comprising applying ultrasonic waves to a forged titanium alloy material produced by the process of claim 1 with a probe having a probe diameter ranging from 5 to 30 mm, to search for a flaw of the forged titanium alloy material in a direction parallel to a direction along which a forging compression reduction of the forged titanium alloy material is largest, wherein the ultrasonic waves have a frequency ranging from 1 to 20 MHz.

* * * * *